(12) United States Patent
Moffitt (10) Patent No.: US 9,572,986 B2
(45) Date of Patent: *Feb. 21, 2017

(54) SYSTEM AND METHOD FOR COMPUTATIONALLY DETERMINING MIGRATION OF NEUROSTIMULATION LEADS

(71) Applicant: BOSTON SCIENTIFIC NEUROMODULATION CORPORATION, Valencia, CA (US)

(72) Inventor: Michael A. Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/727,548

(22) Filed: Dec. 26, 2012

(65) Prior Publication Data
US 2013/0138165 A1    May 30, 2013

Related U.S. Application Data

(63) Continuation of application No. 13/219,269, filed on Aug. 26, 2011, now Pat. No. 8,355,791, and a continuation of application No. 12/899,139, filed on Oct. 6, 2010, now Pat. No. 9,019,427, and a continuation of application No. 11/557,484, filed on Nov. 7, 2006, now Pat. No. 7,831,307.

(51) Int. Cl.
| | | |
|---|---|---|
| *A61N 1/36* | (2006.01) | |
| *A61N 1/08* | (2006.01) | |
| *A61N 1/05* | (2006.01) | |

(52) U.S. Cl.
CPC .............. *A61N 1/36128* (2013.01); *A61N 1/08* (2013.01); *A61N 1/0551* (2013.01); *A61N 1/36071* (2013.01); *A61N 1/36185* (2013.01)

(58) Field of Classification Search
CPC .............................. A61N 1/36128; A61N 1/08
USPC ............................................................ 607/2
See application file for complete search history.

(56) References Cited

U.S. PATENT DOCUMENTS

| | | | |
|---|---|---|---|
| 6,516,227 B1 | 2/2003 | Meadows et al. | |
| 6,609,029 B1 | 8/2003 | Mann et al. | |
| 6,741,892 B1 | 5/2004 | Meadows et al. | |
| 6,993,384 B2 | 1/2006 | Bradley et al. | |
| 7,317,948 B1 * | 1/2008 | King et al. | ........ 607/62 |
| 7,539,538 B2 | 5/2009 | Parramon et al. | |

(Continued)

*Primary Examiner* — Michael Kahelin
(74) *Attorney, Agent, or Firm* — Schwegman Lundberg & Woessner, P.A.

(57) ABSTRACT

A tissue stimulation system and computer software and method of monitoring a neurostimulation lead having a plurality of electrodes implanted within a patient (e.g., adjacent the spinal cord) is provided. Neurostimulation lead models are provided, each of which includes estimated electrical parameter data (e.g., electrical field potential data) corresponding to a predetermined position of the neurostimulation lead. Electrical energy is transmitted to or from the electrodes, and electrical parameter data (e.g., electrical field potential data) is measured in response to the transmitted electrical energy. The measured electrical parameter data is compared with the estimated electrical parameter data of each of the neurostimulation lead models, and a position of the neurostimulation lead is determined based on the comparison.

25 Claims, 7 Drawing Sheets

(56) References Cited

U.S. PATENT DOCUMENTS

| | | | |
|---|---|---|---|
| 7,831,307 B1* | 11/2010 | Moffitt | 607/46 |
| 8,019,427 B2* | 9/2011 | Moffitt | 607/46 |
| 8,355,791 B2* | 1/2013 | Moffitt | 607/46 |
| 2003/0139781 A1* | 7/2003 | Bradley et al. | 607/48 |
| 2005/0065427 A1* | 3/2005 | Magill et al. | 600/407 |
| 2005/0209655 A1 | 9/2005 | Bradley et al. | |
| 2005/0267546 A1 | 12/2005 | Parramon et al. | |
| 2006/0122678 A1 | 6/2006 | Olsen et al. | |
| 2006/0247732 A1 | 11/2006 | Wesselink | |
| 2007/0203542 A1 | 8/2007 | Goetz et al. | |
| 2007/0203545 A1 | 8/2007 | Stone et al. | |

\* cited by examiner

Baseline Positions

FIG. 7

Migrated Positions

|  | | Recording Electrode # | | | | | | | | | | | | | | | |
|---|---|---|---|---|---|---|---|---|---|---|---|---|---|---|---|---|---|
|  | | 1 | 2 | 3 | 4 | 5 | 6 | 7 | 8 | 9 | 10 | 11 | 12 | 13 | 14 | 15 | 16 |
| Transmitting Electrode # | 1 |  |  |  |  |  |  |  |  | i | i | i | i | i | i | i | i |
| | 2 |  |  |  |  |  |  |  |  | i | i | i | i | i | i | i | i |
| | 3 |  |  |  |  |  |  |  |  | i | i | i | i | i | i | i | i |
| | 4 |  |  |  |  |  |  |  |  | i | i | i | i | i | i | i | i |
| | 5 |  |  |  |  |  |  |  |  | i | i | i | i | i | i | i | i |
| | 6 |  |  |  |  |  |  |  |  | i | i | i | i | i | i | i | i |
| | 7 |  |  |  |  |  |  |  |  | i | i | i | i | i | i | i | i |
| | 8 |  |  |  |  |  |  |  |  | i | i | i | i | i | i | i | i |
| | 9 | i | i | i | i | i | i | i | i |  |  |  |  |  |  |  |  |
| | 10 | i | i | i | i | i | i | i | i |  |  |  |  |  |  |  |  |
| | 11 | i | i | i | i | i | i | i | i |  |  |  |  |  |  |  |  |
| | 12 | i | i | i | i | i | i | i | i |  |  |  |  |  |  |  |  |
| | 13 | i | i | i | i | i | i | i | i |  |  |  |  |  |  |  |  |
| | 14 | i | i | i | i | i | i | i | i |  |  |  |  |  |  |  |  |
| | 15 | i | i | i | i | i | i | i | i |  |  |  |  |  |  |  |  |
| | 16 | i | i | i | i | i | i | i | i |  |  |  |  |  |  |  |  |

*FIG. 10*

|  | | Recording Electrode # | | | | | | | | | | | | | | | |
|---|---|---|---|---|---|---|---|---|---|---|---|---|---|---|---|---|---|
|  | | 1 | 2 | 3 | 4 | 5 | 6 | 7 | 8 | 9 | 10 | 11 | 12 | 13 | 14 | 15 | 16 |
| Transmitting Electrode # | 1 |  |  |  |  |  |  |  |  | i |  | i |  | i |  | i |  |
| | 2 |  |  |  |  |  |  |  |  |  |  |  |  |  |  |  |  |
| | 3 |  |  |  |  |  |  |  |  | i |  | i |  | i |  | i |  |
| | 4 |  |  |  |  |  |  |  |  |  |  |  |  |  |  |  |  |
| | 5 |  |  |  |  |  |  |  |  | i |  | i |  | i |  | i |  |
| | 6 |  |  |  |  |  |  |  |  |  |  |  |  |  |  |  |  |
| | 7 |  |  |  |  |  |  |  |  | i |  | i |  | i |  | i |  |
| | 8 |  |  |  |  |  |  |  |  |  |  |  |  |  |  |  |  |
| | 9 | i |  | i |  | i |  | i |  |  |  |  |  |  |  |  |  |
| | 10 |  |  |  |  |  |  |  |  |  |  |  |  |  |  |  |  |
| | 11 | i |  | i |  | i |  | i |  |  |  |  |  |  |  |  |  |
| | 12 |  |  |  |  |  |  |  |  |  |  |  |  |  |  |  |  |
| | 13 | i |  | i |  | i |  | i |  |  |  |  |  |  |  |  |  |
| | 14 |  |  |  |  |  |  |  |  |  |  |  |  |  |  |  |  |
| | 15 | i |  | i |  | i |  | i |  |  |  |  |  |  |  |  |  |
| | 16 |  |  |  |  |  |  |  |  |  |  |  |  |  |  |  |  |

SYSTEM AND METHOD FOR COMPUTATIONALLY DETERMINING MIGRATION OF NEUROSTIMULATION LEADS

RELATED APPLICATION DATA

The present application is a continuation of U.S. patent application Ser. No. 13/219,269, filed Aug. 26, 2011, now issued as U.S. Pat. No. 8,355,791, which is a continuation of U.S. patent application Ser. No. 12/899,139, filed Oct. 6, 2010, now issued as U.S. Pat. No. 8,019,427, which is a continuation of U.S. patent application Ser. No. 11/557,484, filed Nov. 7, 2006, now issued as U.S. Pat. No. 7,831,307, which applications are expressly incorporated herein by reference.

FIELD OF THE INVENTION

The present invention relates to tissue stimulation systems, and more particularly, to systems and methods for determining the migration of neurostimulation leads.

BACKGROUND OF THE INVENTION

Spinal cord stimulation (SCS) is a well-accepted clinical method for reducing pain in certain populations of patients. During SCS, the spinal cord, spinal nerve roots, or other nerve bundles are electrically stimulated using one or more neurostimulation leads implanted adjacent the spinal cord. While the pain-reducing effect of SCS is not well understood, it has been observed that the application of electrical energy to particular regions of the spinal cord induces paresthesia (i.e., a subjective sensation of numbness or tingling) that replaces the pain signals sensed by the patient in the afflicted body regions associated with the stimulated spinal regions. Thus, the paresthesia appears to mask the transmission of chronic pain sensations from the afflicted body regions to the brain.

The working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy.

In a typical procedure, one or more stimulation leads are introduced through the patient's back into the epidural space under fluoroscopy. Stimulation energy may be delivered to the electrodes of the leads during and after the placement process in order to verify that the leads are stimulating the target neural tissue. Stimulation energy is also delivered to the electrodes at this time to formulate the most effective set of stimulus parameters, which include the electrodes that are sourcing (anodes) or returning (cathodes) the stimulation pulses at any given time, as well as the magnitude and duration of the stimulation pulses. During the foregoing procedure, an external trial neurostimulator may be used to convey the stimulation pulses to the lead(s), while the patient provides verbal feedback regarding the presence of paresthesia over the pain area. The stimulus parameter set will typically be one that provides stimulation energy to all of the target tissue that must be stimulated in order to provide the therapeutic benefit (e.g., pain relief), yet minimizes the volume of non-target tissue that is stimulated. Thus, neurostimulation leads are typically implanted with the understanding that the stimulus parameter set will require fewer than all of the electrodes on the leads to achieve the desired paresthesia.

After the lead(s) are placed at the target area of the spinal cord, the lead(s) are anchored in place, and the proximal ends of the lead(s), or alternatively lead extensions, are passed through a tunnel leading to a subcutaneous pocket (typically made in the patient's abdominal area) where a neurostimulator is implanted. The lead(s) are connected to the neurostimulator, which is programmed with the stimulation parameter set(s) previously determined during the initial placement of the lead(s). The neurostimulator may be operated to test the effect of stimulation and, if necessary, adjust the programmed set(s) of stimulation parameters for optimal pain relief based on verbal feedback from the patient. Based on this feedback, the lead position(s) may also be adjusted and re-anchored if necessary. Any incisions are then closed to fully implant the system.

A wide variety of neurostimulation leads have been introduced. One common type of neurostimulation lead is the percutaneous lead, which includes a plurality of spaced electrodes on a small diameter lead body. Percutaneous leads are relatively easy to place because they can be inserted into the epidural space adjacent the spinal cord through a percutaneous needle in a small locally-anesthetized incision while the patient is awake and able to provide feedback. One of the disadvantages of percutaneous leads, however, is that they are prone to migrating in the epidural space, either over time or as a result of sudden flexion movement.

Lead migration may relocate the paresthesia away from the pain site, resulting in the target neural tissue no longer being appropriately stimulated and the patient no longer realizing the full intended therapeutic benefit. With electrode programmability, the stimulation area can often be moved back to the effective pain site without having to reoperate on the patient in order to reposition the lead. Lead migration is, however, not the only reason that the therapeutic effects of a previously effective neurostimulation regimen will diminish or simply disappear, which can make diagnosis difficult. Moreover, even after a physician has determined that lead migration has occurred and that the system must be reprogrammed to accommodate the new positions of the electrodes, conventional neurostimulation systems do not provide the physician with information about the movement of an individual lead, such as how far one lead has moved relative to another lead. Knowledge of relative lead displacement is important, because the resulting misalignment of the anodes and cathodes of the respective leads changes the stimulation pattern, thereby degrading the therapy provided by the SCS. Without such knowledge, the previous stimulation pattern will likely have to be recovered through trial and error and patient feedback, making reprogramming of the electrodes especially difficult.

It is possible to image the patient's spinal column using conventional imaging modalities, such as fluoroscopy, to determine the occurrence and extent of lead migration. However, use of conventional imaging systems, which are often not readily available, is inconvenient and costly. In addition, detection of lead migration via conventional imaging cannot be performed remotely. Furthermore, it may be desirable to automatically program electrodes in response to detection of lead migration. However, the use of conventional imaging modalities to detect lead migration is not suitable for automated electrode programmability.

There, thus, remains a need for an improved method and system for determining the occurrence and extent of neurostimulation lead migration in a patient.

SUMMARY OF THE INVENTION

In accordance with the present inventions, a method of monitoring a neurostimulation lead having a plurality of electrodes implanted within a patient (e.g., adjacent the spinal cord) is provided. The method comprises providing a plurality of neurostimulation lead models, each of which includes estimated electrical parameter data (e.g., electrical field potential data) corresponding to a predetermined position of the neurostimulation lead. Each of the neurostimulation lead models, may be, e.g., an analytical model, spatially discretized model, or an empirical data-based model.

The method further comprises transmitting electrical energy to or from the electrodes, and measuring electrical parameter data (e.g., electrical field potential data) in response to the transmitted electrical energy. Electrical energy may be transmitted between the electrodes and another electrode or other electrodes (e.g., electrodes on another neurostimulation lead, a case of an implantable pulse generator, or other electrodes implanted within the patient). The method further comprises comparing the measured electrical parameter data with the estimated electrical parameter data of each of the neurostimulation lead models. In one method, the comparison is performed computationally; for example, using a comparison function, such as a correlation coefficient function, a least squares based function, or a cross-correlation function.

The method further comprises determining a position of the neurostimulation lead based on the comparison. In one method, the determined position is the predetermined position corresponding to the estimated electrical parameter data that best matches the measured electrical parameter data. In another method, the position of the neurostimulation lead is determined relative to another neurostimulation lead implanted within the patient. For example, if the neurostimulation leads are implanted in a side-by-side arrangement, the determined relative position may be a stagger between the neurostimulation leads. In other methods, the position of the neurostimulation lead may be determined relative to an anatomical feature. An optional method further comprises determining whether the neurostimulation lead has migrated based on the determined position, and taking corrective action (e.g., reprogramming the electrodes) in response to a determination that a neurostimulation lead has migrated.

The afore-described methods can be implemented in a computer readable medium. For example, the medium may contain instructions, which when executed, accesses the neurostimulation lead models, compares the measured electrical parameter data with the estimated electrical parameter data of each of the neurostimulation lead models, and determines the position of the neurostimulation lead based on the comparison.

The afore-described methods can also be implemented in a tissue stimulation system. The system may include the implantable neurostimulation lead, the plurality of neurostimulation lead models, a controller configured for transmitting electrical energy to or from the electrodes and measuring the electrical parameter data in response to the transmitted electrical energy, and a processor configured for comparing the measured electrical parameter data with the estimated electrical parameter data of each of the neurostimulation lead models, and determining the position of the neurostimulation lead based on the comparison.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical and deep brain stimulator, or in any other neural stimulator configured to treat urinary incontinence, sleep apnea, shoulder sublaxation, etc.

Figures 1, 2:
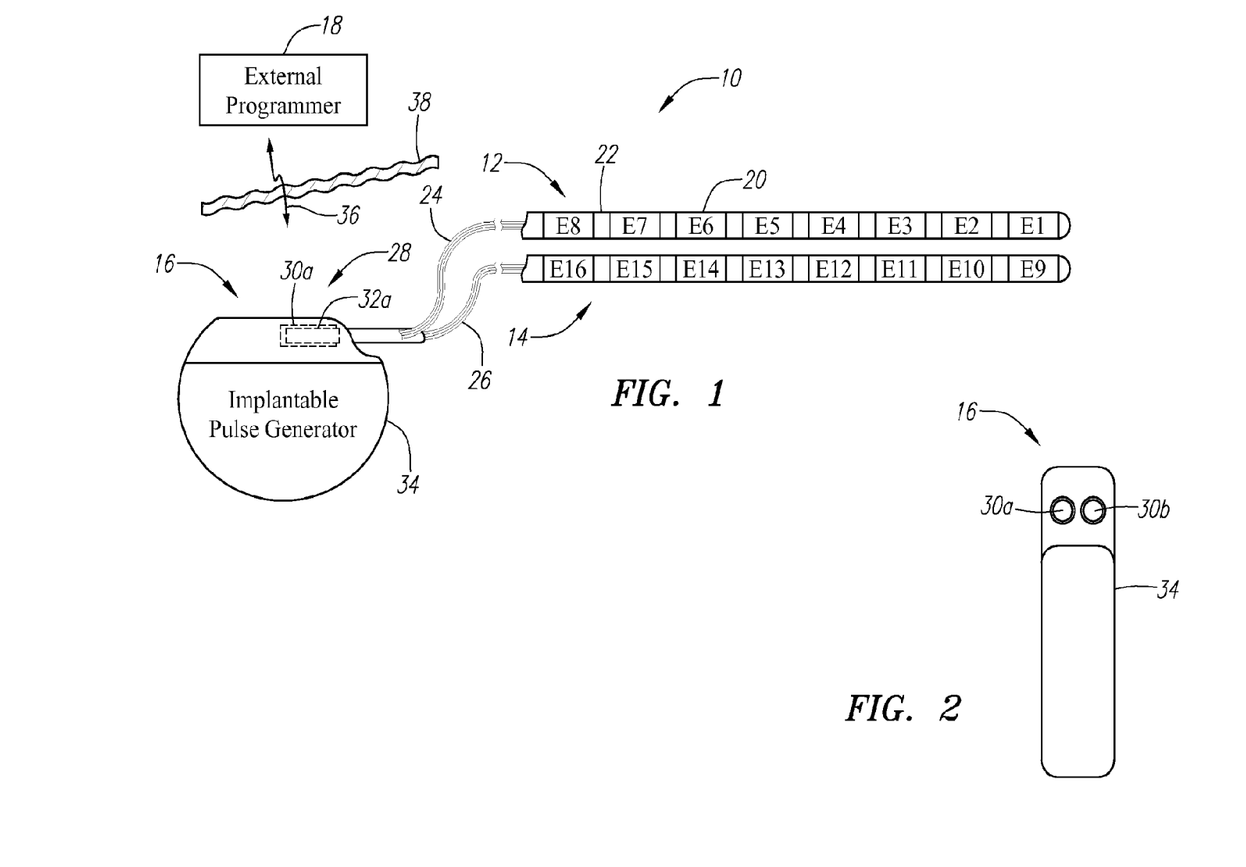
FIG. 1 is plan view of one embodiment of a spinal cord stimulation (SCS) system arranged in accordance with the present inventions.
FIG. 2 is a profile view of an implantable pulse generator (IPG) used in the SCS system of FIG. 1.

Turning first to FIGS. 1 and 2, an exemplary SCS system 10 generally includes first and second implantable neurostimulation leads 12, 14, an implantable pulse generator (IPG) 16, and an external (non-implanted) programmer 18. In the illustrated embodiment, the leads 12, 14 are percutaneous leads and, to that end, both of the leads comprise a plurality of in-line electrodes 20 carried on a flexible body 22. In the illustrated embodiment, the first lead 12 has eight electrodes 20, which are labeled E1-E8, and the second lead 14 includes eight electrodes 20, which are labeled E9-E16. The actual number of leads and electrodes will, of course, vary according to the intended application. The leads 12, 14 are intended to be implanted adjacent to the patient's spinal column through the use of a percutaneous needle or other convention technique. Once in place, the electrodes 20 may be used to supply stimulation energy to the spinal cord or nerve roots.

The IPG 16 is capable of directing electrical stimulation energy to each of the electrodes 20. To that end, the electrodes 20 of the first lead 12 are electrically connected to the IPG 16 by respective signal wires 24 (some of which are not shown) that extend through, or are embedded in, the associated flexible lead body 22. Similarly, the electrodes 20 of the second lead 14 are electrically connected to the IPG 16 by respective wires 26 (some of which are not shown). The signal wires 24, 26 are connected to the IPG 16 by way of an interface 28. The interface 28 may be any suitable device that allows the leads 12, 14 to be removably or permanently electrically connected to the IPG 16. Such an interface may, for example, be an electro-mechanical connector arrangement including lead connectors 30a, 30b within the IPG 16 that are configured to mate with corresponding connectors (only connector 32a is shown) on the corresponding leads 12, 14. Alternatively, the leads 12, 14 can share a single connector that mates with a corresponding connector on the IPG 16. Exemplary connector arrangements are disclosed in U.S. Pat. Nos. 6,609,029 and 6,741,892, which are incorporated herein by reference. The IPG 16 includes an outer case 34 formed from an electrically conductive, biocompatible material, such as titanium and, in some instances, will function as an electrode.

The IPG 16 is typically programmed, or controlled, through the use of the external programmer 18. The external programmer 18 is coupled to the IPG 16 through a suitable communications link (represented by the arrow 36) that passes through the patient's skin 38. Suitable links include, but are not limited to radio frequency (RF) links, inductive links, optical links, and magnetic links. The programmer 18 or other external device may also be used to couple power into the IPG 16 for the purpose of operating the IPG 16 or replenishing a power source, such as a rechargeable battery, within the IPG 16. Once the IPG 16 has been programmed, and its power source has been charged or otherwise replenished, the IPG 16 may function as programmed without the external programmer 18 being present.

With respect to the stimulus patterns provided during operation of the SCS system 10, electrodes that are selected to transmit or receive stimulation energy are referred to herein as "activated," while electrodes that are not selected to transmit or receive stimulation energy are referred to herein as "non-activated." Electrical stimulation will occur between two (or more) electrodes, one of which may be the IPG case 34, so that the electrical current associated with the stimulus has a path from the energy source contained within the IPG case 34 to the tissue and a return path from the tissue to the energy source contained within the case 34. Simulation energy may be transmitted to the tissue in a monopolar or multipolar (e.g., bipolar, tripolar, etc.) fashion.

Monopolar stimulation occurs when a selected one of the lead electrodes 20 is activated along with the case 34, so that stimulation energy is transmitted between the selected electrode 20 and case 24. Bipolar stimulation occurs when two of the lead electrodes 20 are activated as anode and cathode, so that stimulation energy is transmitted between the selected electrodes 20. For example, electrode E3 on the first lead 12 may be activated as an anode at the same time that electrode E11 on the second lead 14 is activated as a cathode. Tripolar stimulation occurs when three of the lead electrodes 20 are activated, two as anodes and the remaining one as a cathode, or two as cathodes and the remaining one as an anode. For example, electrodes E4 and E5 on the first lead 12 may be activated as anodes at the same time that electrode E12 on the second lead 14 is activated as a cathode.

Figures 3, 4:
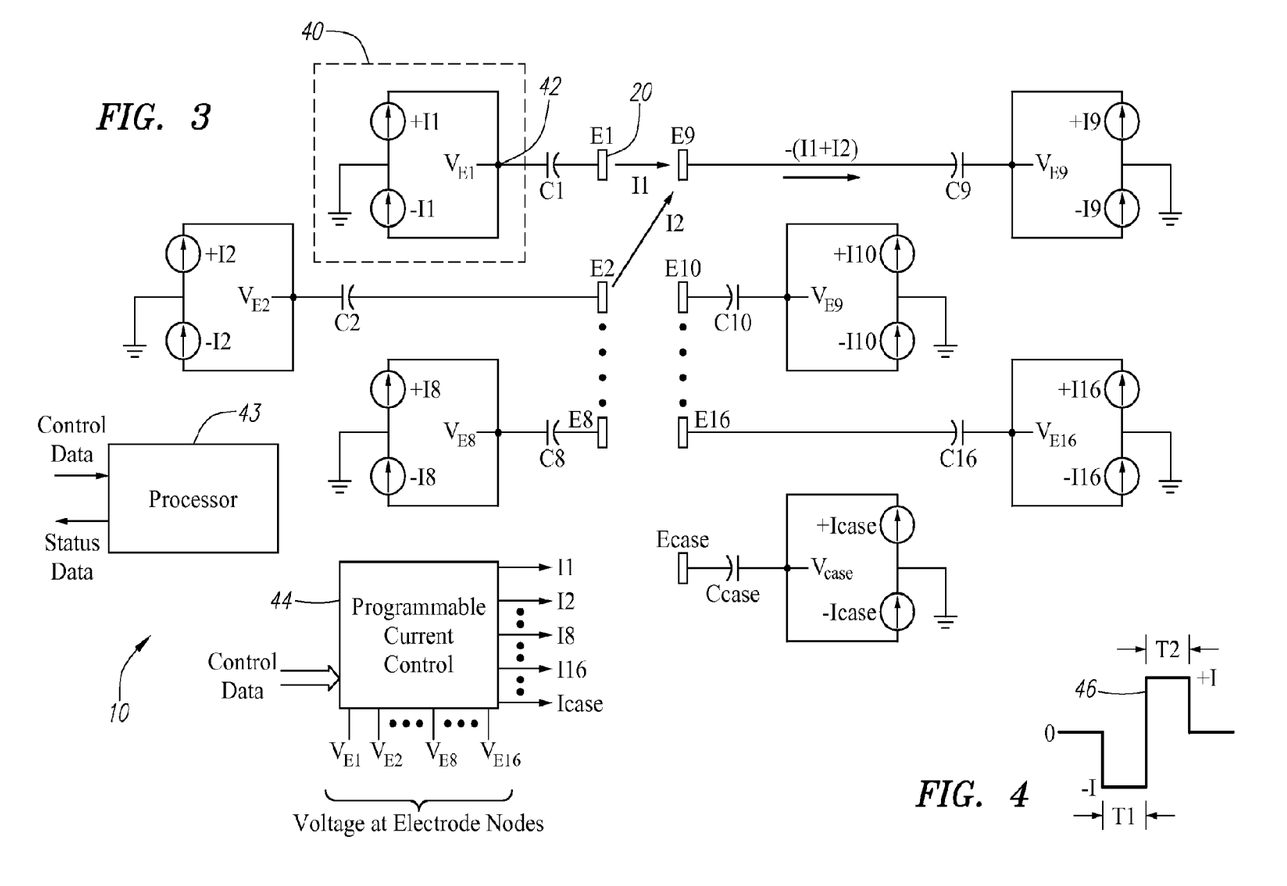
FIG. 3 is a schematic view illustrating current-controlled circuitry of the IPG of FIG. 2.
FIG. 4 is an exemplary stimulation pulse generated by the current-controlled circuitry of FIG. 3.

Turning to FIG. 3, the IPG 16 has a plurality of dual current sources 40. Each dual current source 40 includes a positive current source that can function as an anode (+I1, +I2, +I3, . . . +Icase) to "source" current to a load, as well as a current source that can function as a cathode (−I1, −I2, −I3, . . . −Icase) to "sink" current from the load, through a common node 42. The load is the tissue that resides between the activated electrodes 20, the wires (and other conductive elements), and the coupling capacitor (C1, C2, C3, . . . Ccase) that connects the associated electrode 20 to the common node 49 of the dual current source 40.

The IPG 16 programming will dictate which of the electrodes, i.e., the lead electrodes 20 and the case 34, will act as sources and sinks at any particular time. To that end, the IPG 16 is provided with a processor 43, which receives control data from the external programmer 18 and a programmable current control circuit 44 that, in accordance with the control data, causes selected dual current sources 40 to operate as an anode or a cathode, at specified times, to source or sink current having predetermined amplitude. The processor 43 may also provide status data, such as lead position or migration information (as will be described in further detail below, as well as battery level, etc. The processor 43 and control circuit 44 may be implemented as a microcontroller, which typically comprises a microprocessor and associated logic circuitry, which in combination with control logic circuits, timer logic, and an oscillator and clock circuit, generate the necessary control and status signals which allow the microprocessor to control the operation of the IPG in accordance with the control data. Alternatively, the processor 43 and control circuit 44 may be implemented as a hybrid arranging having a separate digital IC for performing the data processing functions, and an analog IC for controlling the current through the electrodes. In either arrangement, one or more memory devices (not shown) can be used to store control data in the form of programming information, as well as any software instructions utilized to perform the data processing functions herein.

In the illustrated embodiment, where there are eight electrodes 20 on the first lead 12 (labeled E1-E8), eight electrodes on the second lead 14 (E9-E16), and an IPG case 34 that can function as an electrode (labeled Ecase), there are seventeen individually operable dual current sources 40. The control circuit 44, which typically operates in accordance with stored control data that is received from the programmer 18, also turns off the selected dual current sources 40 at specified times. Alternative implementations may, however, employ fewer dual current sources than there are electrodes. Here, at least some of the dual current sources will be connected to more than one electrode through a suitable multiplexer circuit. Alternative implementations may also be configured such that the IPG case 34 only functions as an anode, or such that the IPG case 34 only functions as a cathode.

The control circuit 44 may, in addition, be used to perform various measurement functions. For example, the control circuit 44 may be used to measure the electrode voltage $V_{E1}$, $V_{E2}$, $V_{E3}$ ... $V_{E16}$ at the output node 42 of each dual current source 40, whether the electrode is activated or non-activated. This allows the electrode voltage at the electrode to be measured which, in turn, facilitates lead migration detection, as will be described in further detail below.

Operation of the control circuit 44 may be explained in the context of the following example. Referring further to FIG. 4, the control circuit 44 may be used to simultaneously turn on (or enable) the positive current sources in the dual current sources 40 connected to lead electrodes E1 and E2 during time T1. The negative current source in the dual current source 40 connected to lead electrode E9 is also turned on during time T1. All other current sources are off (or disabled) during the time T1. This causes electrodes E1 and E2 to be activated as anodes at the same time that electrode E9 is activated as a cathode. Currents +I1 and +I2 are sourced from electrodes E1 and E2 at the same time that current −I9 is sunk into electrode E9. The amplitudes of the currents +I1 and +I2 may be any programmed values, and the amplitude of the current −I9 should be equal to −(I1+I2). That is, the current that is sourced is equal to the current that is sunk. After time period T1, the control circuit 44 will typically switch the polarities of the electrodes E1, E2, and E9 during a second time period T2, so that the electrodes E1 and E2 will be activated as cathodes and the electrode E9 will be activated as an anode.

Operating the control circuit 44 in this manner produces a biphasic stimulation pulse 46 illustrated in FIG. 4 that is characterized by a first phase (period T1) of one polarity followed by a second phase immediately or shortly thereafter (period T2) of the opposite polarity. The electrical charge associated with the first phase should be equal to the charge associated with the second phase to maintain charge balance during the stimulation, which is generally considered an important component of stimulation regimes, although this is not required by the present inventions. Charge balance of the biphasic stimulation pulse 46 may be achieved by making the amplitudes of the first and second phases, as well as the periods T1 and T2, substantially equal. Charge balance may also be achieved using other combinations of phase duration and amplitude. For example, the amplitude of the second phase may be equal to one-half of the amplitude of the first phase and the period T2 may be equal to twice the period T1. Rather than maintaining a precise charge-balance, a passive recharge phase may be used to recover all the "recoverable" charge left on the electrode.

Figures 5, 6:
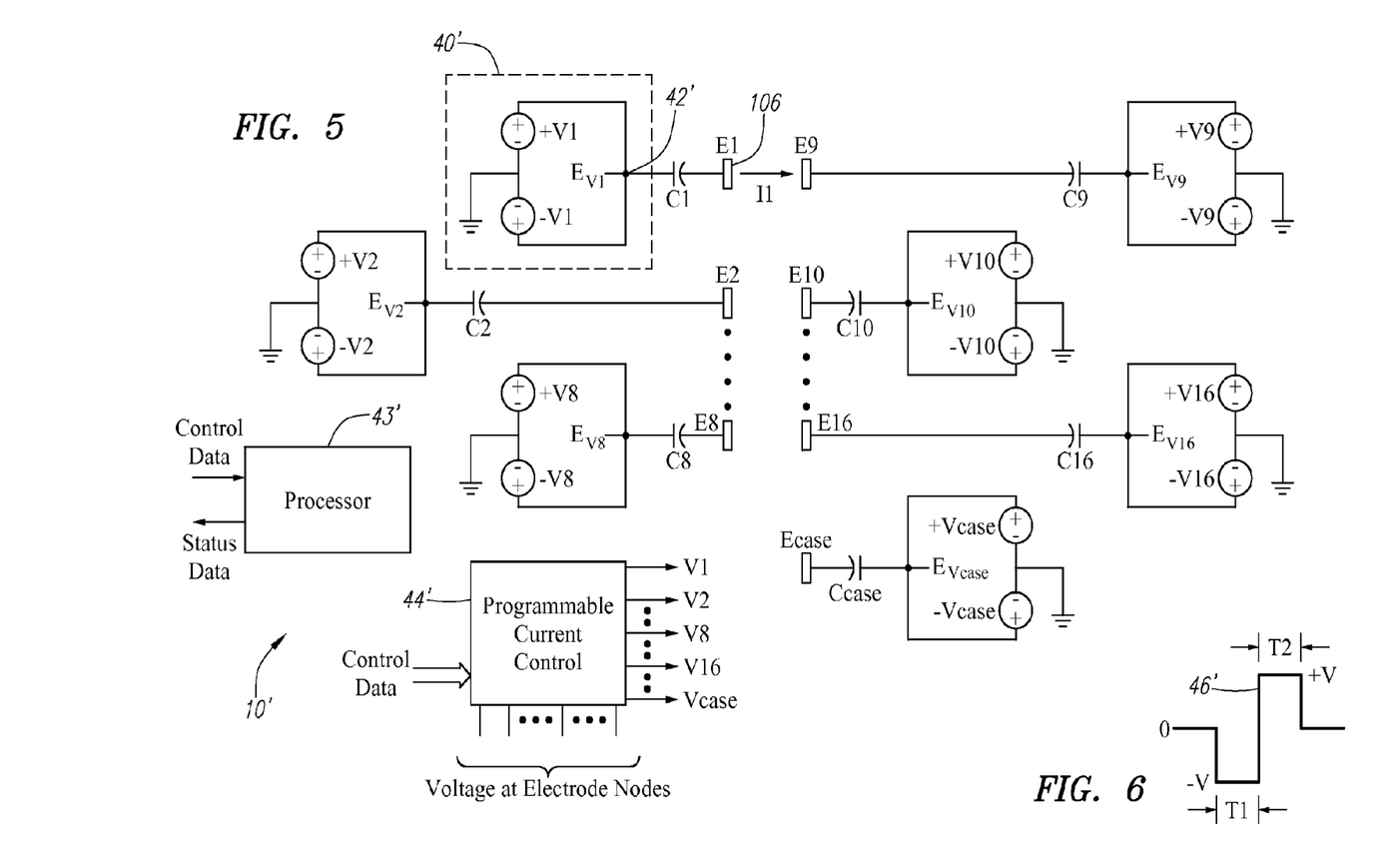
FIG. 5 is a schematic view illustrating alternative voltage-controlled circuitry that can be used in the IPG of FIG. 2.
FIG. 6 is an exemplary stimulation pulse generated by the current-controlled circuitry of FIG. 5.

In an alternative embodiment, the SCS system 10 may include the IPG 16' illustrated in FIG. 5, which includes a plurality of dual voltage sources 40' that are respectively connected to the lead electrodes E1-E16 and the IPG case electrode Ecase. Each dual voltage source 40' applies a programmed voltage to the associated electrode when turned on by way of a node 42' and a coupling capacitor (C1, C2, C3, ... Ccase). Alternative implementations may, however, employ fewer dual voltage sources than there are electrodes. Here, at least some of the dual voltage sources will be connected to more than one electrode should a suitable multiplexer circuit. A processor 43' receives control data from the external programmer 18 and transmits status data to the external programmer 18, and a programmable voltage control circuit 44' controls each of the dual voltage sources 40' and specifies the amplitude, polarity, and duration of the voltage that is applied to the electrodes 20 in accordance with the control data.

The dual voltage sources 40' and control circuit 44' may be used to produce the biphasic stimulation pulse 46' illustrated in FIG. 6 that is characterized by a first phase (period T1) of one polarity followed by a second phase immediately or shortly thereafter (period T2) of the opposite polarity applied between any two electrodes 20. Charge balance of the biphasic stimulation pulse 46' may be achieved by making the amplitudes of the first and second phases, as well as the periods T1 and T2, equal. Charge balance may also be achieved using other combinations of phase duration and amplitude. For example, the amplitude of the second phase may be equal to one-half of the amplitude of the first phase and the period T2 may be equal to twice the period T1. The control circuit 44' may also be used to measure the current flowing to or from each electrode, whether the electrode is activated or not, as well as electrode voltage (EV1-EV16) appearing at the common node 42'. These current and voltage measurements also facilitate lead migration detection.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to leads 12, 14. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 7:
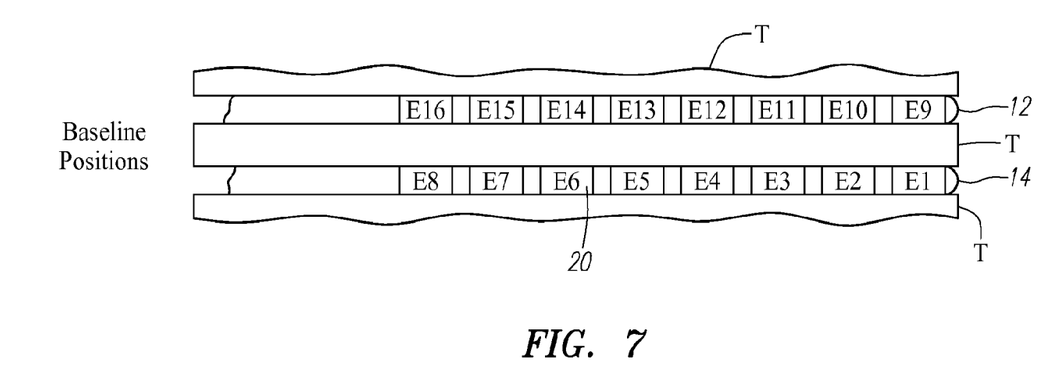
FIG. 7 is a plan view showing the implantation of neurostimulation leads used in the SCS system of FIG. 1, wherein the leads are particularly shown in their baseline positions.
Figure 8:
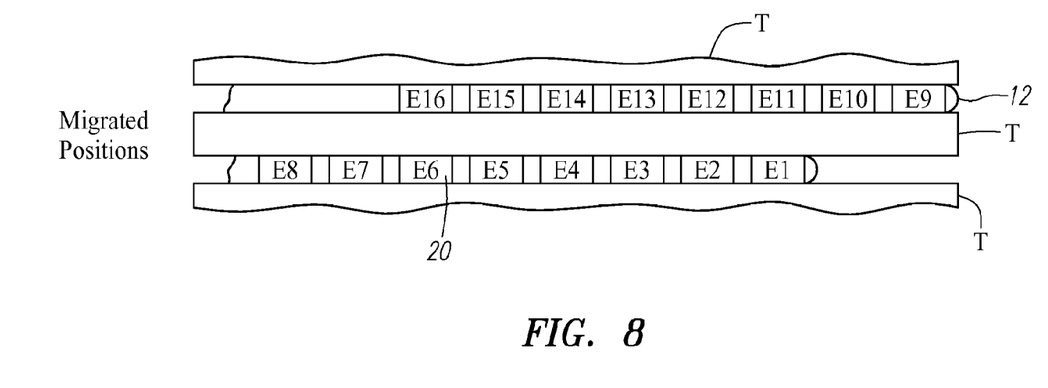
FIG. 8 is a plan view showing the implantation of neurostimulation leads used in the SCS system of FIG. 1, wherein one of the leads is particularly shown in their migrated positions.

The SCS system 10 is capable of detecting the occurrence and extent of post-implantation migration of the neurostimulation leads 12, 14 (i.e., movement of the leads 12, 14 relative to the underlying tissue); for example, from a base line lead arrangement, wherein the leads 12, 14 have been initially implanted within tissue T in a parallel and non-staggered relationship, as shown in FIG. 7, to a migrated lead arrangement, wherein the leads 12, 14 are in a parallel, but staggered relationship (two electrode offset), as shown in FIG. 8. Notably, while the baseline lead arrangement has been shown as being non-staggered, conceivably, a baseline lead arrangement can be non-staggered, and the migrated lead arrangement staggered, ultimately depending on the manner in which the electrodes 20 are programmed. Thus, the SCS system 10 will be capable of detecting the occurrence and extent of lead migration for any situation in which one of the leads moves from an intended position dictated by the programmed electrodes.

Figure 9:
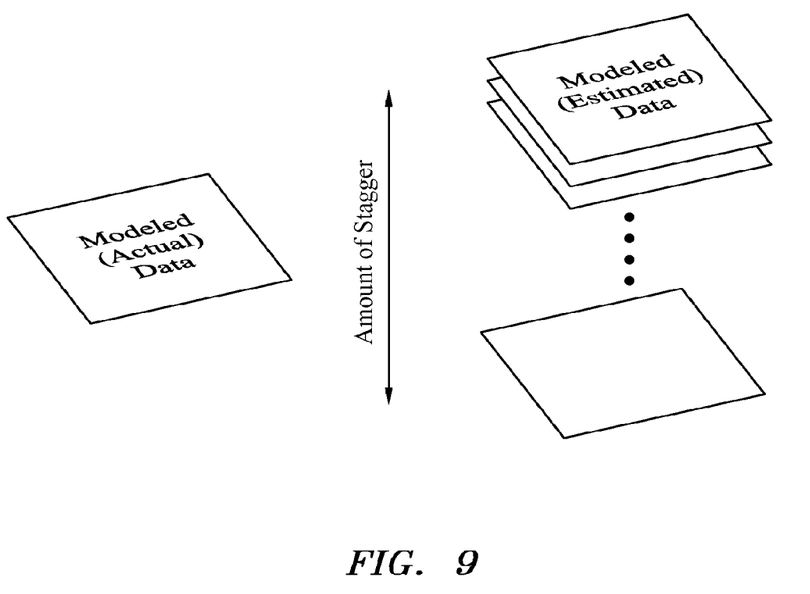
FIG. 9 is a perspective view of a comparison between actual data measured by the SCS system of FIG. 1 and a plurality of neurostimulation lead models having estimated data stored in the SCS system of FIG. 1.

Referring to FIG. 9, the lead migration detection process is accomplished by generating actual electrical parameter data indicative of the current position, orientation, and/or geometry of the leads 12, 14 and computationally comparing that data to a plurality of previously generated neurostimulation lead models, and in particular, estimates of the electrical parameter data corresponding to different predetermined positions, orientations and/or geometries of the leads 12, 14. The position, orientation and/or geometry corresponding to the model having the estimated electrical parameter data that best matches the measured (i.e., actual) electrical parameter data will be deemed the position, orientation and/or geometry of the leads 12, 14. The measured electrical parameter data and the lead models may be stored and processed by the IPG control circuit 44 (or 44'), by the external programmer 18, by some combination thereof, or the like.

In the illustrated embodiment, the SCS system 10 determines the relative positions between the leads 12, 14, and in particular, the stagger between the leads 12, 14. Thus, each model may be generated by estimating the electrical parameter data at each of a plurality of staggered positions between the leads 12, 14. Optionally, the SCS system 10 may determine the relative orientation between the leads 12, 14, and in particular, the angle between the leads 12, 14. In this case, each model may be generated by also estimating the electrical parameter data at each of a plurality of staggered lead position and angle combinations. In other optional embodiments, the SCS system 10 may even determine the geometry (e.g., curvature) of the leads 12, 14. Thus, in this case, each model may be generated by also estimating the electrical parameter data at each of a plurality of staggered lead position, angle, and curvature combinations.

Notably, it may be necessary to constrain the lead models to provide a unique solution. That is, determining the position, angle, and curvature of a neurostimulation lead may present electrical inverse problems, which absent constraints, typically do not results unique solutions. The lead models should not be over-constrained, such that they do not yield any useful information (i.e., information that cannot be used to determine migration of the leads), and should not be under-constrained, such that there is not a unique solution (i.e., more than one lead model will contain substantially the same electrical parameter data). Thus, it may be preferred that the lead models be constrained, such that only relative position between the leads 12, 14 (i.e., stagger) be determined. In this case, each lead model assumes that the leads 12, 14 have a rectilinear geometry and are parallel to each other. In this case, it is ensured that the lead models return a unique solution. While the SCS system 10 may not be able to detect lateral migration of the leads 12, 14, which may otherwise be detected if the relative orientation of the leads 12, 14 were modeled, much of the problems associated with lead migration result from movement of one of the leads 12, 14 along its length, which will be capable of being detecting by determining the lead stagger.

In the illustrated embodiment, the electrical parameter data that is measured (and thus modeled) is voltage potential data of an electrical field generated by selected ones of the lead electrodes 20 (individually identified as E1-E16) and recorded at other selected ones of the lead electrodes 20. This may be accomplished in one of a variety of manners. For example, anytime after the leads 12, 14 have been properly positioned within tissue ("proper" positioning varies from patient to patient), an electrical field may be generated by sourcing a current from a selected one of the electrodes 20 and sunk at the IPG outer case 34. Alternatively, multipolar configurations (e.g., bipolar or tripolar) may be created between the lead electrodes 20. It should be noted that the current used for generating the electrical field may be a sub-threshold current pulse (e.g., 1 mA for 20 µs) that will not cause stimulation or substantially drain the IPG battery. Alternatively, an electrode that is sutured (or otherwise permanently or temporarily attached (e.g., an adhesive or gel-based electrode) anywhere on the patient's body may be used in place of the case IPG outer case 34 or lead electrodes 20.

In either case, while a selected one of the electrodes E1-E16 is activated to generate the electrical field, a selected one of the electrodes E1-E16 (different from the activated electrode) is operated to record the voltage potential of the electrical field. This process can be repeated for different electrical field generating electrodes and different voltage potential recording electrodes. In the preferred embodiment, selected ones of the electrodes 20 are sequentially operated to generate electrical fields. In one embodiment, selected ones of the electrodes 20 are sequentially operated to record the field potentials, in which case, a single recording circuit will suffice. In another embodiment, multiple recording circuits can be employed, in which case, selected ones of the electrodes 20 can be simultaneously operated to record the field potentials, thereby reducing processing time.

In any event, for each electrical field generated by one of the lead electrodes 20, selected others of the lead electrodes 20 are used to record the voltage potentials of the electrical field, thereby creating a two-dimensional array of data having electrical field generating electrodes in one dimension of the data array, and recording electrodes in the other dimension of the data array. For example, referring to FIG. 9, an exemplary two-dimensional array of recorded field potential data is shown, wherein the rows represent the particular electrodes E1-E16 used to create the electrical fields, and columns represent the particular electrodes E1-E16 used to record the voltage potentials of the electrical fields. Thus, the two-dimensional array contains a recorded field potential for each pair of field generating/recording electrodes (e.g., (E1,E10), (E9, E2), etc.).

While all of the electrodes E1-E16 can be used create electrical fields and record voltage potentials, thereby creating 240 electrode combinations (electrodes cannot be used to both generate electrical fields and record voltage potentials, and therefore, a number of electrode combinations (in this case, 16) cannot be used) and 240 corresponding field potential data items, the combinations of electrodes E1-E16 most relevant to determining movement of the leads 12, 14 are used in the illustrated embodiment. For example, in the illustrated embodiment, the SCS system 10 determines the relative positions between the leads 12, 14, and in particular, the stagger between the leads 12, 14. Optionally, the SCS system 10 may even determine the relative orientation between the leads 12, 14, and in particular, the angle between the leads 12, 14. Thus, only voltage potentials recorded on a lead opposite to the lead generating the electrical field will be useful in determining stagger, or optionally the angle between the leads 12, 14.

Figure 10:
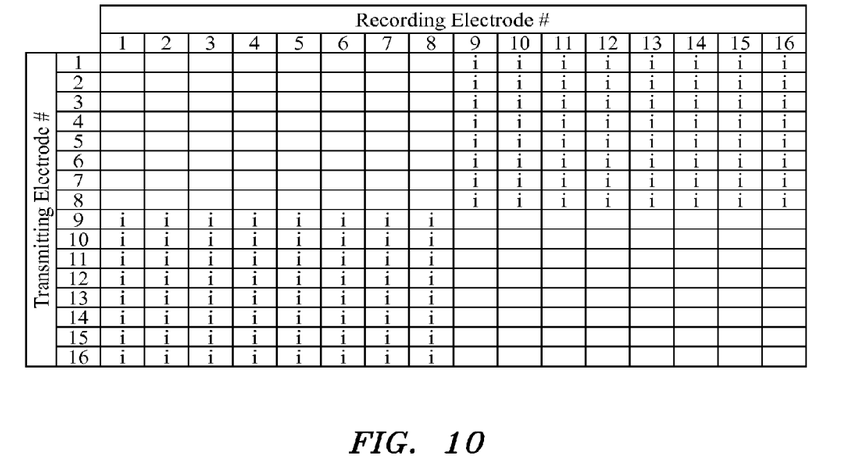
FIG. 10 is a one embodiment of a table containing a two-dimensional array of data measured in the SCS system of FIG. 1.

In this case, the most pertinent combinations of electrodes E1-E16 are those combinations that includes electrodes on different leads 12, 14; that is, one of the electrodes E1-E8 on the first lead 12 as one of the electrical field generating electrode or voltage potential recording electrode, and one of the electrodes E9-E16 on the second lead 14 as the other of the electrical field generating electrode or voltage potential recording electrode. Thus, as illustrated in FIG. 10, the two-dimensional array includes voltage potential entries corresponding to electrode combinations on opposite leads, as represented by the regions indicated with "i".

Figure 11:
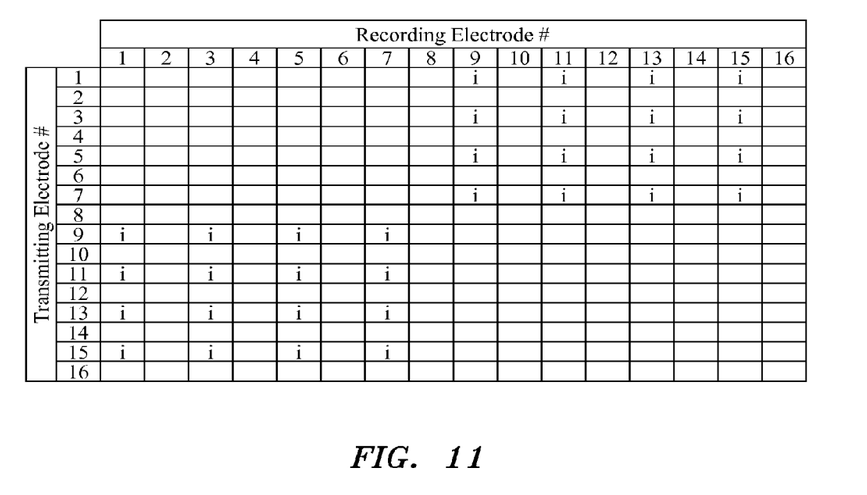
FIG. 11 is an alternative embodiment of a table containing a two-dimensional array of data measured in the SCS system of FIG. 1.

Optionally, the SCS system 10 may determine the geometry of one or both of the leads 12, 14 (e.g., the curvature). In this case, combinations of electrodes E1-E16 on the same lead, as well as combinations of electrodes E1-E16 on opposite leads, will provide useful information. It should be appreciated that if processing time or data storage becomes an issue, the resolution of the electrodes E1-E16 used to generate electrical fields and record voltage potentials may be decreased if some accuracy can be sacrificed. For example, instead of using all electrodes E1-E16 to generate electrical fields and record voltage potentials, every other ones of the electrodes E1-E16 (e.g., only the odd numbered electrodes) may be used to generate electrical fields and record voltage potentials, as illustrated in FIG. 11. In this case, the amount of data stored and processed will be reduced by seventy-five percent.

The amount of data stored and processed may also be reduced by using only unidirectional data, since generating an electrical field on a first electrode (e.g., E1) and recording the voltage potential on a second electrode (e.g., E13) should yield the same result as generating an electrical field on the second electrode (e.g., E13) and recording the voltage potential on the first electrode (e.g., E1). In this case, roughly half of the data contained in a two-dimensional electrode array may be considered redundant (the diagonal and either the upper-right or lower-left triangles would be considered useful information). When the concept of using only unidirectional data is applied to the electrode arrays of FIGS. 10 and 11, which assume that the relative positions of leads will be assessed (i.e., cross-lead data will be critical (i.e., sourcing/sinking current on a contact of one lead and measuring data, such as a field potential, on a contact of a different lead), where same-lead data will not be as useful). As a result, the amount of data stored and processed, after removing same lead data, will be further reduced by 50%; that is, only the data "i" currently shown in the top-right quadrants of FIGS. 10 and 11 will be collected (although only the data "I" currently shown in the bottom-left quadrant can be collected if, instead, the electrodes E9-E16 are used to generate electrical fields, and electrodes E1-E8 are used to record voltage potentials.

Significantly, each of the lead models would similarly be represented as two-dimensional arrays; that is, two-dimensional arrays wherein the rows represent the electrodes E1-E16 used to create the electrical fields, and columns represent the electrodes E1-E16 used to record the voltage potentials of the electrical fields. The lead models may, e.g., be based on an analytical model, spatially discretized model (e.g., finite element, boundary element), or an empirical data-based model. In the case of an analytical model, the tissue may be modeled as a homogenous mass, and the stimulating electrode may be modeled as a point source. In the case of a spatially discretized model, the different tissues, such as fat, collagen, bone, ligament, the white and gray matter of the spinal cord, and dura can be discretely modeled.

It should be noted that, while the present invention lends itself well to the determination of relative positions, or optionally orientations, between leads, the SCS system 10 may be modified, so that the absolute position and/or orientation of a lead can be determined. In this case, one or more electrodes (not shown), such as a bone screw electrode or otherwise an electrode fixed relative to an anatomical feature (such as a bone), can be used. The fixed electrode(s) can either generate the electrical fields (with the lead electrodes 20 recording the voltage potentials) and/or record the voltage potentials (with the lead electrodes 20 generating the electrical fields). In this manner, the absolute position and/or orientation (i.e., relative to anatomical feature), can be determined.

While voltage potential data has been described as the electrical parameter data that is measured, it should be appreciated that other types of electrical parameter data, such as impedance data, can be measured. For example, the impedance between selected bipolar pairs of the electrodes E1-E16 may be measured, e.g., by transmitting a constant current between the selected bipolar pairs, measuring the voltage potential at the bipolar pairs, and calculating the impedance based on the constant current value and voltage potential measurements. Further details describing the measurement of electrical parameter data, such as voltage potential data and impedance data, are disclosed in U.S. Pat. No. 6,993,384, which is expressly incorporated herein by reference.

To determine which of the modeled estimated electrical parameter data best matches the measured electrical parameter data, the data can be computationally compared with each other using any one of a variety of comparison functions.

For example, one comparison function that can be used is a correlation coefficient function, such as a Pearson Correlation Coefficient function, which can be expressed as the following equation:

$$r = \frac{\sum_i (AD_i - M_{AD})(ESTi - M_{EST})}{sqrt\left(\sum_i (AD_i - M_{AD}) \sum_i (ESTi - M_{EST})^2\right)},$$

where r is the coefficient, AD represents the actual (measured) data set (e.g., the two-dimensional arrays illustrated in FIG. 10 or 11), EST represents the model-based estimate of the data set (e.g., the two-dimensional modeled arrays corresponding to the arrays of FIG. 10 or 11), M represents the mean of the data set (either actual or modeled), and i represents a single element of the data set (either actual or modeled) (i.e., the data generated by a single combination of electrodes (e.g., E1, E9). Advantageously, the correlation coefficient is not sensitive to magnitude scaling, and ranges from −1 (perfect inverse correlation) to 1 (perfect correlation). With this function, we seek a maximum—the highest correlation between the actual data and the model-based estimated of the data.

Another comparison function that can be used is a least squares based function, and in particular, a sum of squared differences function, which can be expressed as the following equation:

$$SSD = \sum_i ((AD_i - EST_i)^2),$$

where
SSD is the sum of squared difference, and AD, EST, and i have been defined above. The SSD function measures the difference between the actual data and an instance of the model-based estimate of the data. With this function, we seek a minimum—the instance of the model yielding estimates that are the least different from the actual data. Other comparison functions, including cross-correlation functions, wavelet functions, and associated matching measures, may be alternatively used.

Figure 12:
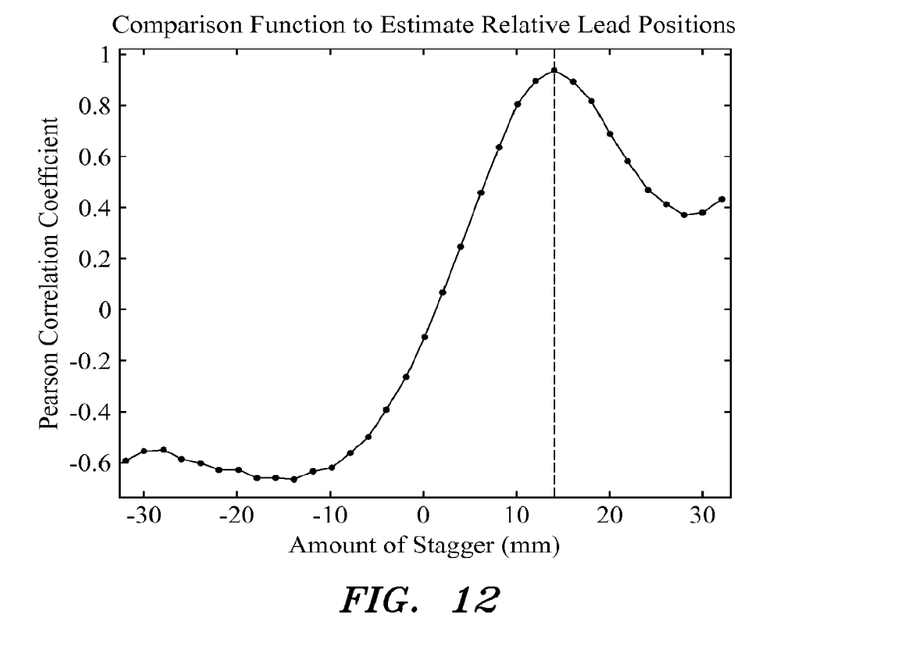
FIG. 12 is a plot of a Pearson Correlation Coefficient function used to compare measured voltage potential data with estimated voltage potential data contained in neurostimulation lead models.
Figure 13:
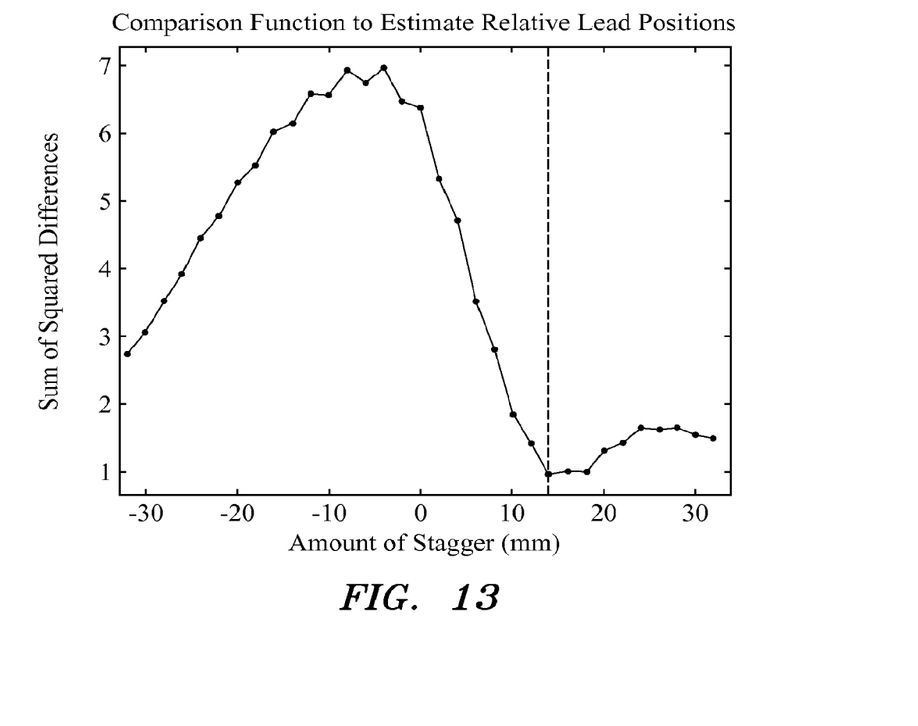
FIG. 13 is a plot of a sum of squared differences function used to compare measured voltage potential data with estimated voltage potential data contained in neurostimulation lead models.

FIG. 12 shows the results of a data comparison using a Pearson Correlation Coefficient function, with the x-axis representing a staggered lead position, and the y-axis representing the coefficient value. FIG. 13 shows the results of a data comparison using the SSD function, with the x-axis representing a staggered lead position, and the y-axis representing the SSD value. The plots of FIGS. 12 and 13 were created using Matlab to both generate the "actual voltage potential data" and the model-based estimates of the voltage potential data. In particular, using the electrode combinations illustrated in FIG. 10, the "actual voltage potential data" was modeled using an analytical point source model with leads separated by 5 mm, staggered by 14 mm, and with Gaussian white noise (stdev=25 mv). The maximum voltage of the "actual voltage potential data" was 497.4 mV in the absence of noise. Using the same electrode combinations, models of estimated voltage potential data were created using an analytical point source model with leads separated by 2 mm over thirty-three different staggered lead positions. The "actual voltage potential data set" was then computationally compared to these models using the Pearson Coefficient function to create the plot of FIG. 12 and using the SSD function to create the plot of FIG. 13.

As can be seen, each data point in the plot of FIG. 12 represents a staggered lead position with a corresponding coefficient value, and each data point in the plot of FIG. 13 represents a staggered lead position with a corresponding SSD value. As would be expected, the particular data point having the staggered lead position of 14 mm corresponds to the highest coefficient value in the plot of FIG. 12 and the lowest SSD value in the plot of FIG. 13. In both cases, the estimated position of 14 mm will correctly be selected as the determined staggered position of the leads.

The corrective action that may be taken after it has been determined that one or more of the leads 12, 14 in the SCS system 10 has moved generally falls into two categories—(1) surgical removal or repositioning and (2) reprogramming. Surgical removal or repositioning will typically be employed when it has been determined that one or more of the leads 12, 14 has moved too far to make reprogramming a viable option. If, for example, the therapeutic regimen required that an electrode be located in the baseline location of electrode E2 on lead 12 shown in FIG. 7, the therapeutic regimen could not be performed once lead 12 migrated to the location shown in FIG. 8 because there is no long any electrode in that location. Surgical removal may also be required if one or more of the electrodes are damaged or fails.

With respect to reprogramming, individuals information concerning the actual movement (or lack of movement) of each lead 12, 14 will allow reprogramming to proceed in a far more efficient manner than would be the case if the entity tasked with reprogramming (i.e., a physician or the SCS system 10) merely know that at least one of the leads 12, 14 have moved due to a change in their relative positions. Assuming, for example, that the leads 12, 14 illustrated in FIG. 7 were employed in a therapeutic regimen that involved sourcing and sinking stimulation pulses from electrodes E4, E5, and E6 on lead 12 and electrodes E13 and E14 on lead 14, after lead 12 moved to the position illustrated in FIG. 8, and it was determined that only lead 12 moved and that it moved toward the IPG 16 a distance corresponding to two electrodes, the therapeutic regimen may be reprogrammed by simply substituting electrodes E2, E3, and E4, respectively, for electrodes E4, E5, and E6.

Reprogramming may be performed automatically or by a clinician. Automatic reprogramming, which is especially useful when lead migration is being continuously monitored, could be truly automatic (i.e., it would happen without the patient's knowledge). Alternatively, the IPG 16 could provide the patient with an indication that at least one lead 12, 14 has moved and provide the patient the option of trying the automatically reprogrammed stimulation regimen or simply reporting the lead migration to the clinician. Reprogramming by the clinician, either in response to a notification from the IPG 16 or patient complaint, would typically involve allowing the external programmer 18 to modify (or simply suggest a modification of) the therapeutic regimen based on the lead migration data from the IPG 16. Alternatively, the lead repositioning is recorded for the clinician to review for use during reprogramming, thereby reducing the amount of clinician time (and expense) required to reprogram the therapeutic regimen, as well as the likelihood that an expensive fluoroscopic procedure will be required.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of monitoring a neurostimulation lead having a plurality of electrodes implanted within a patient, the method comprising:
    providing a plurality of sets of estimated electrical parameter data, each set corresponding to a predetermined relative position of the neurostimulation lead;
    transmitting electrical energy to or from the electrodes;
    measuring electrical parameter data in response to the transmitted electrical energy;
    comparing the measured electrical parameter data with the estimated electrical parameter data of each of the sets; and
    determining a position of the neurostimulation lead based on the comparison.

2. The method of claim 1, wherein the position of the neurostimulation lead is determined relative to another neurostimulation lead implanted within the patient.

3. The method of claim 2, wherein the neurostimulation leads are implanted in a side-by-side arrangement.

4. The method of claim 3, wherein the determined relative position is a stagger between the neurostimulation leads.

5. The method of claim 1, wherein the position of the neurostimulation lead is determined relative to an anatomical feature.

6. The method of claim 1, wherein the neurostimulation lead is implanted adjacent a spinal cord of the patient.

7. The method of claim 1, wherein the estimated electrical parameter data and the measured electrical parameter data are electrical field potential data.

8. The method of claim 1, wherein the determined position is the predetermined position corresponding to the estimated electrical parameter data that best matches the measured electrical parameter data.

9. The method of claim 1, wherein the comparison is performed computationally.

10. The method of claim 9, wherein the comparison is computationally performed using a comparison function selected from the group consisting of a correlation coefficient function, a least squares based function, and a cross-correlation function.

11. The method of claim 1, further comprising providing a plurality of neurostimulation lead models, the plurality of lead models respectively including the plurality of sets of electrical parameter data, wherein each of the neurostimulation models is selected from the group consisting of an analytical model, a spatially discretized model, and an empirical data-based model.

12. The method of claim 1, further comprising determining whether the neurostimulation lead has migrated based on the determined position.

13. The method of claim 12, further comprising taking corrective action in response to a determination that the neurostimulation lead has migrated.

14. The method of claim 13, wherein the corrective action comprises reprogramming the electrodes.

15. A tissue stimulation system, comprising:
an implantable neurostimulation lead having a plurality of electrodes;
memory;
a plurality of sets of estimated electrical parameter data stored in the memory, each set corresponding to a predetermined position of the neurostimulation lead;
a controller configured for transmitting electrical energy to or from the electrodes and measuring electrical parameter data in response to the transmitted electrical energy; and
a processor configured for comparing the measured electrical parameter data with the estimated electrical parameter data of each of the sets, and determining a position of the neurostimulation lead based on the comparison.

16. The tissue stimulation system of claim 15, further comprising another implantable neurostimulation lead, wherein the position of the neurostimulation lead is determined relative to the other neurostimulation lead.

17. The tissue stimulation system of claim 16, wherein the determined relative position is a stagger between the neurostimulation leads.

18. The tissue stimulation system of claim 17, wherein the position of the neurostimulation lead is determined relative to an anatomical feature.

19. The tissue stimulation system of claim 15, wherein the estimated electrical parameter data and the measured electrical parameter data are electrical field potential data.

20. The tissue stimulation system of claim 15, wherein the determined position is the predetermined position corresponding to the estimated electrical parameter data that best matches the measured electrical parameter data.

21. The tissue stimulation system of claim 15, wherein the comparison is performed computationally.

22. The tissue stimulation system of claim 21, wherein the comparison is computationally performed using a comparison function selected from the group consisting of a correlation coefficient function, a least squares based function, and a cross-correlation function.

23. The tissue stimulation system of claim 15, further comprising a plurality of neurostimulation lead models stored in the memory, the plurality of lead models respectively including the plurality of sets of electrical parameter data, each of the neurostimulation lead models is selected from the group consisting of an analytical model, a spatially discretized model, and an empirical data-based model.

24. The tissue stimulation system of claim 15, wherein the processor is further configured for determining whether the neurostimulation leads has migrated based on the determined position.

25. The tissue stimulation system of claim 24, wherein the processor is further configured for reprogramming the electrodes in response to a determination that the neurostimulation lead has migrated.

* * * * *